(12) United States Patent
Lee et al.

(10) Patent No.: US 7,157,576 B2
(45) Date of Patent: Jan. 2, 2007

(54) CRYSTALLINE ACID SALTS OF CEFDINIR AND PROCESS FOR PREPARING CEFDINIR USING SAME

(75) Inventors: Gwan-Sun Lee, Seoul (KR);
Young-Kil Chang, Seoul (KR);
Hong-Sun Kim, Seoul (KR);
Chul-Hyun Park, Seongnam-si (KR);
Gha-Seung Park, Goyang-si (KR);
Cheol-Kyung Kim, Namyangju-si (KR)

(73) Assignee: Hanmi Pharm. Co., Ltd. (KR)

( * ) Notice: Subject to any disclaimer, the term of this patent is extended or adjusted under 35 U.S.C. 154(b) by 295 days.

(21) Appl. No.: 10/479,291

(22) PCT Filed: Jun. 5, 2002

(86) PCT No.: PCT/KR02/01064

§ 371 (c)(1),
(2), (4) Date: Nov. 25, 2003

(87) PCT Pub. No.: WO02/098884

PCT Pub. Date: Dec. 12, 2002

(65) Prior Publication Data

US 2004/0210049 A1    Oct. 21, 2004

(30) Foreign Application Priority Data

Jun. 5, 2001    (KR) ................. 2001-31339

(51) Int. Cl.
*C07D 501/22* (2006.01)
(52) U.S. Cl. .................................. 540/222
(58) Field of Classification Search ............ None
See application file for complete search history.

(56) References Cited

U.S. PATENT DOCUMENTS

| 4,260,543 | A | * | 4/1981 | Miller | 540/350 |
|---|---|---|---|---|---|
| 4,713,451 | A | * | 12/1987 | Leanza et al. | 540/350 |
| 4,748,238 | A | * | 5/1988 | Shih | 540/350 |
| 4,888,344 | A | * | 12/1989 | Sunagawa et al. | 514/210.13 |
| 4,990,613 | A | * | 2/1991 | Kumagai et al. | 540/350 |
| 5,424,306 | A | * | 6/1995 | Kawamoto et al. | 514/210.12 |
| 6,924,279 | B1 | * | 8/2005 | Kawamoto et al. | 514/210.13 |
| 2004/0242556 | A1 | * | 12/2004 | Dandala et al. | 514/202 |
| 2005/0255370 | A1 | * | 11/2005 | Figueroa et al. | 429/40 |
| 2006/0025586 | A1 | * | 2/2006 | Kremminger et al. | 540/222 |
| 2006/0074236 | A1 | * | 4/2006 | Pozzi et al. | 540/222 |

FOREIGN PATENT DOCUMENTS

| EP | 0 304 019 A2 | | 8/1988 |
|---|---|---|---|
| JP | 09-110869 | * | 4/1997 |
| WO | WO 2004016623 A1 | * | 2/2004 |
| WO | WO 2004056835 A1 | * | 7/2004 |

OTHER PUBLICATIONS

Translation of JP 09-110869.*
Lin, Hecheng Huaxue 9(5) 383-385 2001 and translation.*
"Plastic" <http://64.233.161.104/search?q-32 cache:4a4pLQ6fpbUJ:secure.britanica.com/eb/article-82464>, downloaded from the internet Jul. 6, 2006.*
"General Effects of Ageing on Textiles" <http://aic.stanford.edu/jaic/articles/jaic25-01-004_1.html>, downloaded from the internet Jul. 6, 2006.*
Zeng et al. Phys. Rev. Lett. 86, 4875-4878 (2001).*

* cited by examiner

*Primary Examiner*—Mark L. Berch
(74) *Attorney, Agent, or Firm*—Anderson Kill & Olick, PC

(57) ABSTRACT

High purity cefdinir is prepared in a high yield by a process comprising the steps of: treating a crystalline salt of a cefdinir intermediate with a formic acid-sulfuric acid mixture or a formic acid-methanesulfonic acid mixture to obtain a crystalline salt of cefdinir and reacting the crystalline salt with a base in a solvent.

9 Claims, 4 Drawing Sheets

CRYSTALLINE ACID SALTS OF CEFDINIR AND PROCESS FOR PREPARING CEFDINIR USING SAME

FIELD OF THE INVENTION

The present invention relates to crystalline acid salts of cefdinir, a process for their preparation and a process for preparing cefdinir using the salts.

BACKGROUND OF THE INVENTION

In the preparation of cefdinir, a cephalosporin antibiotic, deprotection reaction of the carboxy-protected cefdinir is usually conducted in a strongly acidic medium, e.g., trifluoroacetic acid (U.S. Pat. No. 4,559,334). Such a strong acid treatment step, however, generates undesired by-products including E-isomer (anti-form) of cefdinir; and, as a result, many methods have been developed to remove the contaminant E-isomer. For example, the method disclosed in International Publication No. WO98/45299 comprises converting crude cefdinir into a salt of dicyclohexylamine, removing the impurity and reconverting the purified salt to cefdinir. However, this multi-step method is inefficient and gives a low productivity.

U.S. Pat. No. 4,935,507 discloses a method of producing crystalline cefdinir, which comprises the steps of reacting amorphous cefdinir with an acid in a solvent and adding a non-polar solvent thereto to precipitate an acid-added salt of cefdinir, e.g., cefdinir.HCl, cefdinir.$H_2SO_4$ and cefdinir.$CH_3SO_3H$. However, the acid-added salt formed as an intermediate in this method is an amorphous bulky material which has poor stability and shows low purity.

Thus, there has continued to exist a need to develop an improved process for preparing a highly pure cefdinir.

SUMMARY OF THE INVENTION

Accordingly, it is a primary object of the present invention to provide an efficient method of preparing high purity cefdinir.

It is another object of the present invention to provide a crystalline acid salt of cefdinir with high purity which can be advantageously used in the preparation of high purity cefdinir.

It is a further object of the present invention to provide a process for the preparation of the crystalline acid salt of cefdinir.

In accordance with one aspect of the present invention, there is provided a crystalline acid salt of cefdinir of formula (I):

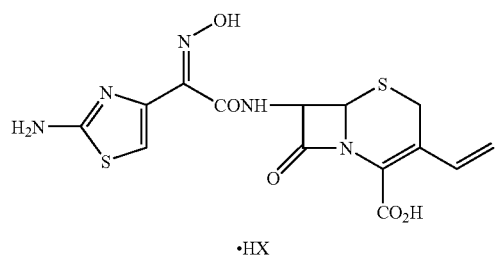

(I)

wherein HX is $H_2SO_4$ or $CH_3SO_3H$.

In accordance with another aspect of the present invention, there is provided a method of preparing a compound of formula (I) which comprises reacting a cefdinir intermediate of formula (II) with a formic acid-sulfuric acid mixture or a formic acid-methanesulfonic acid mixture in a solvent:

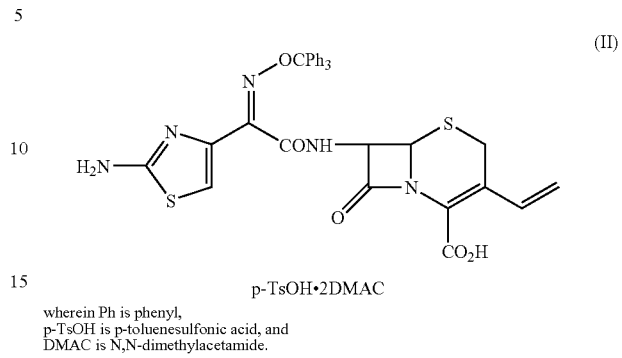

(II)

p-TsOH·2DMAC wherein Ph is phenyl,
p-TsOH is p-toluenesulfonic acid, and
DMAC is N,N-dimethylacetamide.

In accordance with a still another aspect of the present invention, there is provided a method of preparing cefdinir of formula (III) which comprises reacting the compound of formula (I) with a base in a solvent:

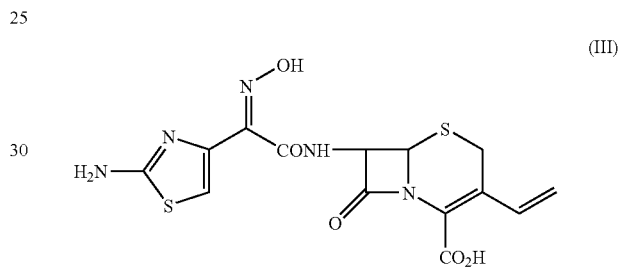

(III)

BRIEF DESCRIPTION OF THE DRAWINGS

The above and other objects and features of the present invention will become apparent from the following description of the invention taken in conjunction with the following accompanying drawings, which respectively show.

DETAILED DESCRIPTION OF THE INVENTION

Figure 1:
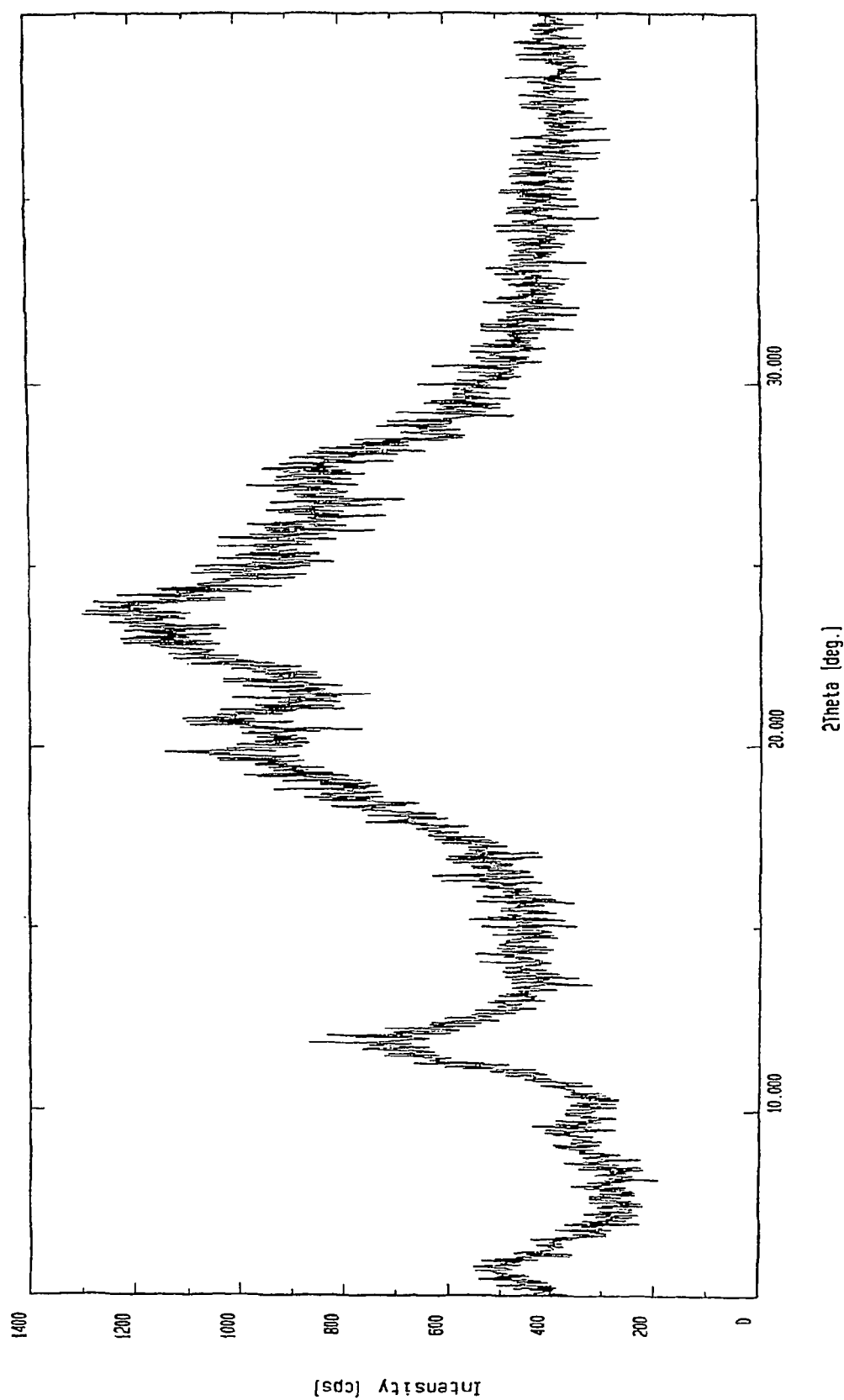
FIGS. 1 and 3: powder X-ray diffraction patterns of cefdinir.$H_2SO_4$ and cefdinir.$CH_3SO_3H$, respectively, prepared in accordance with the prior art.

The crystalline acid salt of cefdinir of formula (I) may be prepared by treating a cefdinir intermediate of formula (II) with a formic acid-sulfuric acid mixture or a formic acid-methanesulfonic acid mixture in a suitable solvent.

The cefdinir intermediate of formula (II) used in the present invention may be prepared using the reactions and techniques described in U.S. Pat. No. 6,093,814.

The content of formic acid used in the present invention is 99 to 70%, preferably 95 to 80% and remainder is water. The amount of the formic acid used may range from 5 to 30 equivalents, preferably from 10 to 20 equivalents, based on the amount of the cefdinir intermediate of formula (II).

Further, the amount of the sulfuric acid or methanesulfonic acid used in the inventive process may range from 2 to 5 equivalents, preferably from 2.5 to 3.5 equivalents, based on the amount of the cefdinir intermediate of formula (II).

Exemplary solvents which may be suitably used in the above reaction are any one selected from the group consisting of acetonitrile, diethyl ether, tetrahydrofuran, 1,4-dioxane, ethyl acetate, methylene chloride, chloroform, isopropanol, ethanol and a mixture thereof, wherein acetonitrile is preferred. The amount of the solvent used may range from 2 to 20 volumes (ml/g), preferably from 4 to 10 volumes (ml/g) based on the amount of the cefdinir intermediate of formula (II).

The above reaction in accordance with the present invention may be performed at a temperature ranging from 5 to 40° C., preferably from 10 to 30° C., for a period ranging from 8 to 20 hours.

The acid salts of cefdinir prepared in accordance with the present invention are novel crystalline monosulfuric acid and monomethanesulfonic acid salt of cefdinir, unlike the amorphous acid salts disclosed in the prior art.

Further, highly pure cefdinir of formula (III) can be obtained easily by simply treating the crystalline acid salt of cefdinir of formula (I) with a base in a suitable solvent.

Exemplary solvents which may be suitably used in the above reaction are any one selected from the group consisting of water, ethanol, methanol, acetonitrile, 1,4-dioxane, isopropanol, acetone, methylethylketone, methylisobutylketone and a mixture thereof, wherein a mixture of water and ethanol is preferred. The amount of the solvent used may range from 5 to 30 volumes (ml/g), preferably from 10 to 20 volumes (ml/g) based on the amount of the acid salt of cefdinir of formula (I).

Exemplary bases which may be suitably used in the above reaction include aqueous ammonia, sodium hydroxide, potassium hydroxide, sodium carbonate, potassium carbonate, sodium bicarbonate, potassium bicarbonate, sodium acetate, potassium acetate, sodium ethylhexanoate, triethylamine, diisopropylethylamine, dimethylethylamine, tributylamine, pyridine, dimethylbenzylamine, triethanolamine, dimethylaminopyridine and a mixture thereof, wherein sodium acetate is preferred. The base may be used in an amount ranging from 1 to 3 equivalents based on the amount of the compound of formula (I) to adjust the pH at 1.5 to 3.5.

Acid addition salt of cefdinir in accordance with the inventive process is characteristically formed in the reaction solution while deprotecting a cefdinir intermediate of formula (II). More characteristically, the inventive process described above gives a higher yield and a higher purity of crystalline acid salt of cefdinir as compared with any of the conventional methods. Specifically, the purity is more than 99% and contamination of E-isomer (anti-form) is surprisingly less than 0.1%. Thus, according to the inventive process, acid addition salt of cefdinir is highly crystalline and shows high stability, from which highly pure cefdinir can be obtained in a high yield.

The following Reference Example and Examples are intended to further illustrate the present invention without limiting its scope; and the experimental methods used in the present invention can be practiced in accordance with the Reference Example and Examples given below, unless otherwise stated.

Further, percentages given below for solid in solid mixture, liquid in liquid, and solid in liquid are on the bases of wt/wt, vol/vol and wt/vol, respectively, unless specifically indicated otherwise.

REFERENCE EXAMPLE 1

Preparation of 7β-[(Z)-2-(2-aminothiazol-4-yl)-2-trityloxyiminoacetamido]-3-vinyl-3-cephem-4-carboxylic acid.p-TsOH.2DMAC 8.0 g of 7-amino-3-vinyl-3-cephem-4-carboxylic acid and 21.5 g of (Z)-(2-aminothiazol -4-yl)-2-trityloxyiminoacetic acid 2-benzothiazolylthioester were suspended in 80 ml of N,N-dimethylacetamide and 16.8 ml of tri-n-butylamine was added thereto. Then, the mixture was stirred for 1 hour while maintaining the temperature at 15 to 20° C. 240 ml of diethyl ether was added thereto and stirred for 30 minutes, and then filtered through a cellite. Added to the filtrate was 20.2 g of p-toluenesulfonic acid.monohydrate dissolved in 40 ml of methanol and the resulting solution was stirred for 2 hours at room temperature. After 160 ml of diethyl ether was added thereto, the resulting solution was further stirred for 1 hour at room temperature, cooled to 0 to 5° C., stirred for 1 hour and filtered. The precipitate thus obtained was washed sequentially with 50 ml of N,N-dimethylacetamide/diethyl ether (1:5, v/v) and 50 ml of diethyl ether, and then dried to obtain 32.3 g (Yield: 93%) of the title compound as a pale yellow solid.

HPLC purity: 99.2%

H-NMR(δ, MeOH-$d_4$): 2.08(6H,s,$CH_3CO$), 2.31(3H,s,$CH_3Ph$), 2.94(3H,s,—N—$CH_3$), 3.01(3H, s,—N—$CH_3$), 3.7(2H,brd s,C-2), 4.96(1H,s,C-6), 5.22~5.34(2H,m,—CH═$CH_2$), 5.67(1H,s,C-7), 6.67(1H,s,aminothiazol ring-H), 7.06~7.29(20H,m,—$NH_2$,—CH═$CH_2$, $Ph_3$C—, $CH_3Ph$), 7.52(2H,d, 2,$CH_3Ph$)

EXAMPLE 1

Preparation of 7β-[(Z)-2-(2-aminothiazol-4-yl)-2-hydroxyimino acetamido]-3-vinyl-3-cephem-4-carboxylic acid.$H_2SO_4$ 40 g of 7β-[(Z)-2-(2-aminothiazol-4-yl)-2-trityloxyiminoacetamido]-3-vinyl -3-cephem-4-carboxylic acid.p-TsOH.2DMAC obtained in Reference Example 1 was suspended in 200 ml of acetonitrile. 20 ml of 90% formic acid and 6.0 ml of 98% sulfuric acid were added thereto and then reacted for 20 hours while maintaining the temperature at 15 to 20° C. The precipitate thus obtained was filtered and washed sequentially with 100 ml of acetonitrile and 100 ml of diethyl ether, and then dried to obtain 18.2 g (Yield: 91%) of the title compound as a pale yellow crystalline solid.

HPLC purity: 99.9%

E—isomer: 0.08%

Melting point: 180° C. (decomposition)

IR($cm^{-1}$,KBr): 3391, 3225, 3116, 1774, 1651, 1526, 1164, 1042, 877, 672, 589, 570

H-NMR(δ,DMSO-$d_6$): 3.62, 3.85(2H,ABq,C-2), 5.24 (1H,d,C-6), 5.35(1H,d,—CH═$CH_2$), 5.62(1H,d,—CH═$CH_2$), 5.78~5.83(1H,m,C-7), 6.88(1H,s aminothiazol ring-H), 6.90~7.00(1H,m,—CH═$CH_2$), 9.81(1H,d,—NH—)

Figure 2:
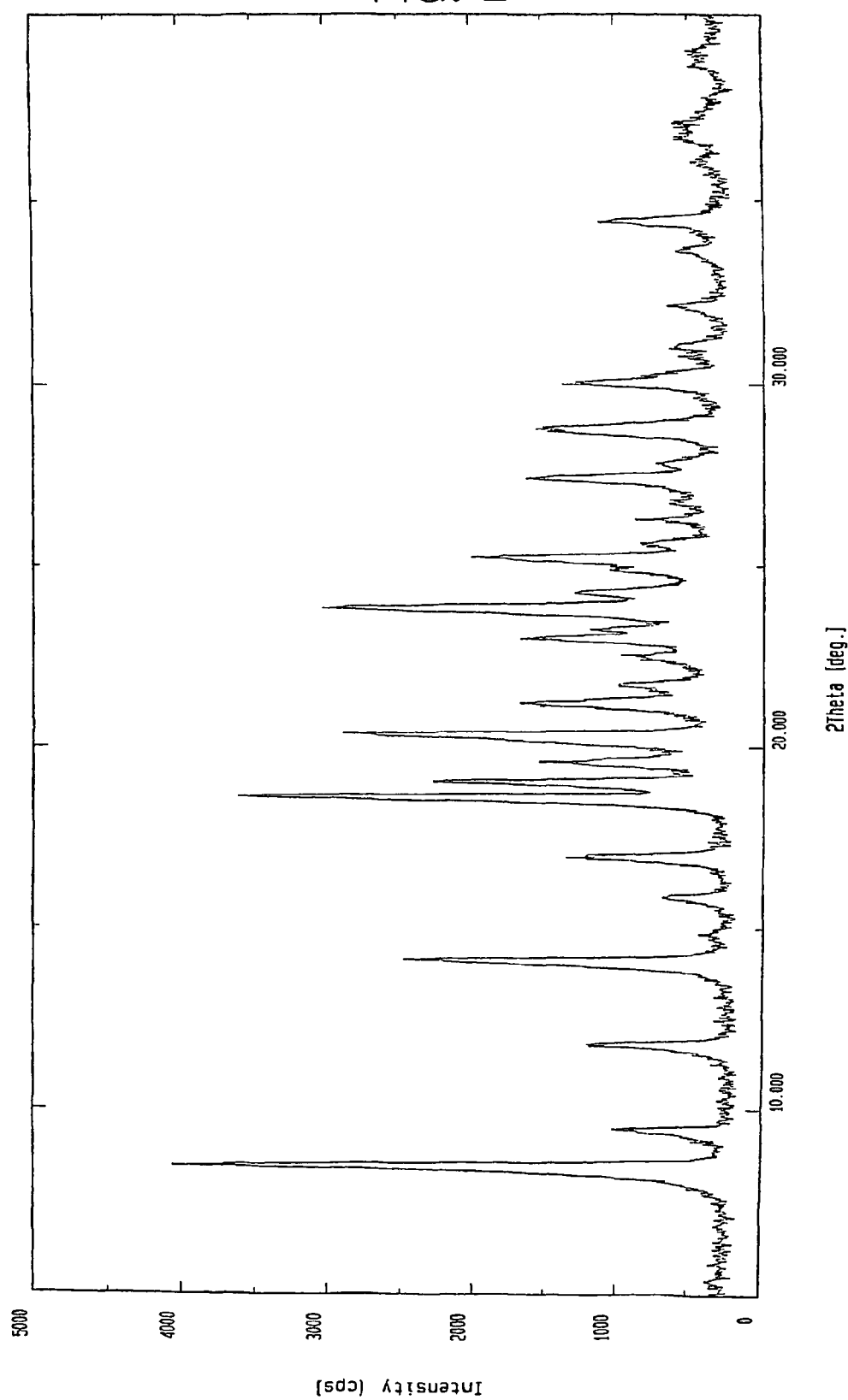
FIGS. 2 and 4: powder X-ray diffraction patterns of cefdinir.$H_2SO_4$ and cefdinir.$CH_3SO_3H$, respectively, prepared in accordance with the inventive method.

The X-ray diffraction pattern in FIG. 2 shows that the cefdinir.$H_2SO_4$ thus obtained is highly crystalline, which should be compared with the broad peak pattern for the cefdinir sulfate prepared in accordance with the conventional method (FIG. 1). The peaks observed in FIG. 2 are summarized in Table 1.

TABLE 1

| 2θ | d | I/I₀ | 2θ | d | I/I₀ |
|---|---|---|---|---|---|
| 8.4 | 10.5 | 100 | 20.3 | 4.4 | 73 |
| 9.4 | 9.4 | 21 | 21.2 | 4.2 | 39 |
| 11.8 | 7.5 | 28 | 23.0 | 3.9 | 38 |
| 14.1 | 6.3 | 61 | 23.8 | 3.7 | 80 |
| 17.0 | 5.2 | 30 | 25.2 | 3.5 | 48 |
| 18.6 | 4.8 | 95 | 27.4 | 3.3 | 38 |
| 19.0 | 4.7 | 55 | 28.7 | 3.1 | 36 |
| 19.6 | 4.5 | 32 | 30.0 | 3.0 | 30 | d: lattice parameter; and
I/I₀: relative peak intensity

EXAMPLE 2

Preparation of 7β-[(Z)-2-(2-aminothiazol-4-yl)-2-hydroxyimino acetamido]-3-vinyl-3-cephem-4-carboxylic acid.CH₃SO₃H 100 g of 7β-[(Z)-2-(2-aminothiazol-4-yl)-2-trityloxyiminoacetamido]-3-vinyl-3-cephem-4-carboxylic acid.p-TsOH.2DMAC obtained in Reference Example 1 was suspended in 200 ml of acetonitrile. 40 ml of 85% formic acid and 18.5 ml of methanesulfonic acid were added thereto, and then reacted for 20 hours while maintaining the temperature at 20 to 25° C. The precipitate thus obtained was filtered and washed sequentially with 100 ml of acetonitrile and 100 ml of diethylether, and then dried to obtain 43.9 g (Yield 88%) of the title compound as a pale yellow crystalline solid.

HPLC purity: 99.8%
E—isomer: 0.12%
Melting point: 210° C. (decomposition)
IR(cm⁻¹,KBr): 3285, 3231, 1775, 1684, 1636, 1527, 1356, 1195, 1145, 1043, 782, 590
H-NMR(δ,DMSO-d₆): 2.37(3H,s,CH₃S), 3.58, 3.82(2H, ABq,C-2), 5.21(1H,d,C-6), 5.32(1H,d,—CH=CH₂), 5.60(1H,d,—CH=CH₂), 5.75~5.80(1H,m,C-7), 6.85(1H,s, aminothiazol ring-H), 6.86~6.96(1H,m,—CH=CH₂), 9.83(1H, d,—NH—)

Figure 3:
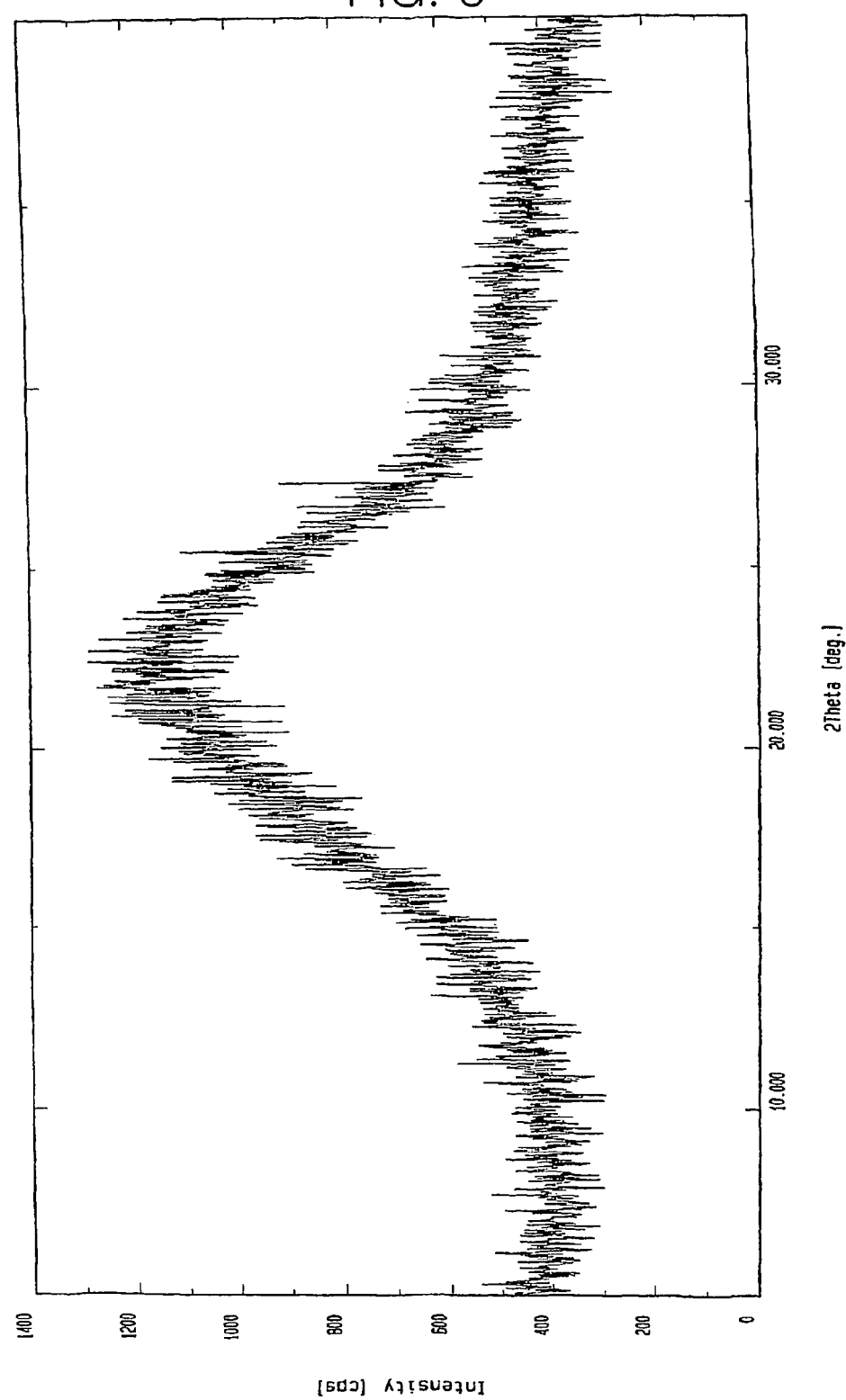
Figure 4:
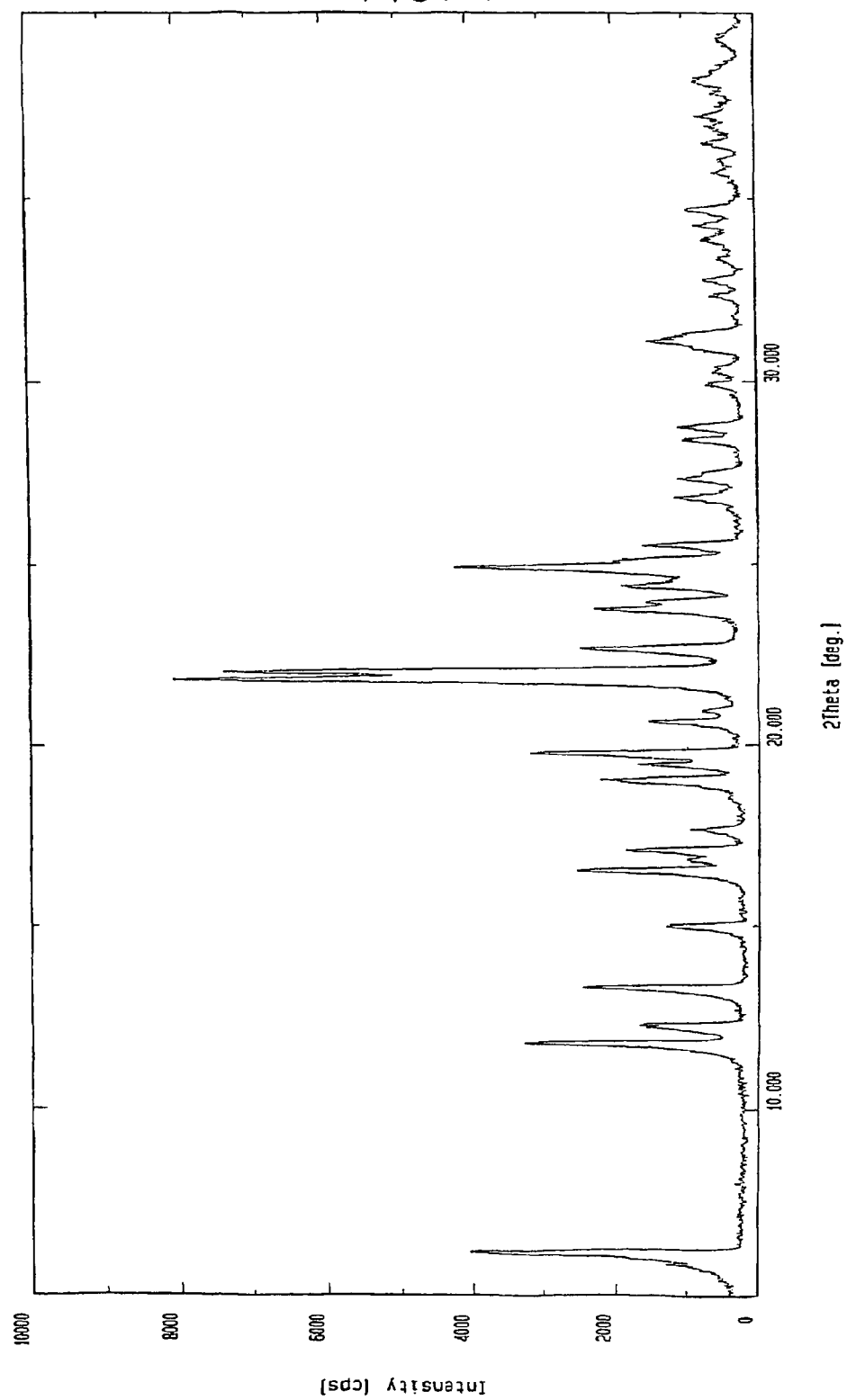

The highly crystalline nature of the cefdinir.CH₃SO₃H is verified by the powder X-ray diffraction pattern shown in FIG. 4. The cefdinir.CH₃SO₃H prepared in accordance with the prior art method is amorphous as showed in FIG. 3. The peaks observed in FIG. 4 are summarized in Table 2.

TABLE 2

| 2θ | d | I/I₀ | 2θ | d | I/I₀ |
|---|---|---|---|---|---|
| 6.1 | 14.4 | 44 | 21.8 | 4.1 | 100 |
| 11.8 | 7.5 | 38 | 22.0 | 4.0 | 90 |
| 13.3 | 6.7 | 28 | 22.6 | 3.9 | 30 |
| 16.5 | 5.4 | 30 | 23.7 | 3.8 | 27 |
| 17.0 | 5.2 | 21 | 24.3 | 3.7 | 22 |
| 19.0 | 4.7 | 26 | 24.9 | 3.6 | 52 |
| 19.7 | 4.5 | 38 | 25.5 | 3.5 | 17 |
| 20.6 | 4.3 | 17 | 31.1 | 2.9 | 17 |

EXAMPLE 3

Preparation of 7β-[(Z)-2-(2-aminothiazol-4-yl)-2-hydroxyimino acetamido]-3-vinyl-3-cephem-4-carboxylic acid (cefdinir)

3.0 g of 7β-[(Z)-2-(2-aminothiazol-4-yl)-2-hydroxyiminoacetamido]-3-vinyl -3-cephem-4-carboxylic acid.H₂SO₄ obtained in Example 1 was suspended in 30 ml of water and adjusted to pH 3.4 to 3.6 with 1.0 g of sodium bicarbonate. The resulting solution was stirred at a temperature ranging from 30 to 40° C. for 30 minutes, cooled to 0 to 5° C., and then stirred for 30 minutes. The precipitate thus obtained was filtered and washed with 30 ml of distilled water, and then dried to obtain 1.40 g (Yield 87%) of the title compound as a pale yellow crystalline solid.

HPLC purity: 99.9%
E—isomer content: 0.06%
H-NMR(δ,DMSO-d₆): 3.57, 3.85(2H,ABq,C-2), 5.20 (1H,d,C-6), 5.32(1H,d,—CH=CH₂), 5.61(1H,d,—CH=CH₂), 5.79~5.83(1H,m,C-7), 6.69(1H,s,aminothiozol ring-H), 6.89~6.98(1H,m,—CH=CH₂), 7.14(2H, brd s, —NH2), 9.79(1H,d,—NH—).

EXAMPLE 4

Preparation of 7β-[(Z)-2-(2-aminothiazol-4-yl)-2-hydroxyamino acetamido]-3-vinyl-3-cephem-4-carboxylic acid (cefdinir)

5.0 g of 7β-[(Z)-2-(2-aminothiazol-4-yl)-2-hydroxyiminoacetamido]-3-vinyl -3-cephem-4-carboxylic acid.CH₃SO₃H obtained in Example 2 was suspended in 50 ml of ethanol and adjusted to pH 3.4 to 3.6 by adding triethylamine thereto dropwise. The resulting solution was stirred at a temperature ranging from 30 to 35° C. for 30 minutes. The precipitate thus obtained was filtered, dispersed in a mixture of 30 ml of distilled water and 10 ml of ethanol, stirred at a temperature ranging from 30 to 35° C. for 30 minutes, filtered, washed with 20 ml of distilled water, and then dried to obtain 3.31 g (Yield: 82%) of the title compound as a pale yellow crystalline solid.

HPLC purity: 99.8%
E—isomer content: 0.08%
H-NMR data of this product were identical with those of the compound prepared in Example 3.

While the invention has been described with respect to the above specific embodiments, it should be recognized that various modifications and changes may be made to the invention by those skilled in the art which also fall within the scope of the invention as defined by the appended claims.

The invention claimed is:

1. A method of preparing the crystalline sulfuric acid salt of cefdinir of formula (I) which comprises reacting a cefdinir intermediate of formula (II) with a formic acid-sulfuric acid mixture in a solvent:

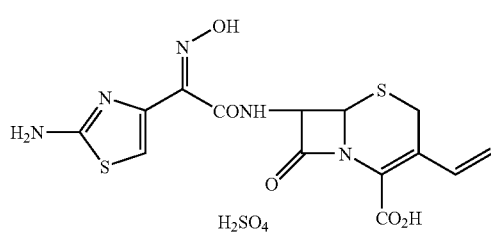

(I)

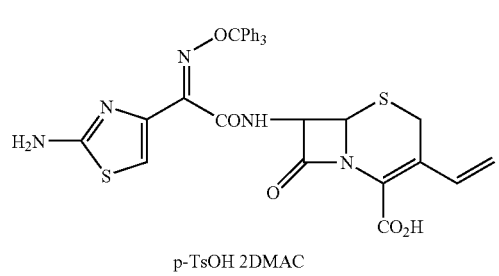

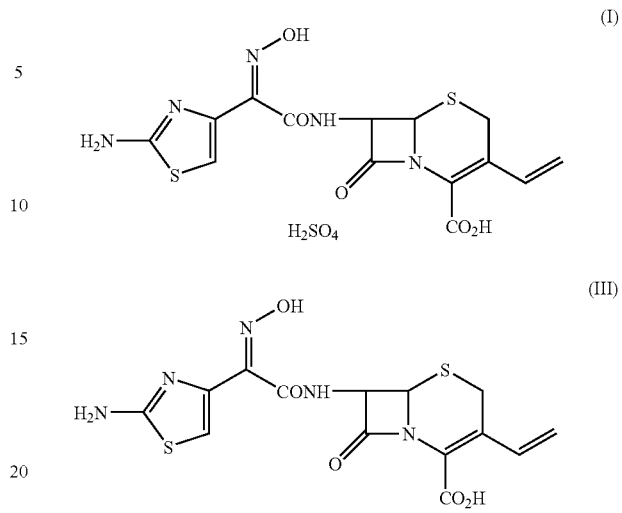

wherein Ph is phenyl, p-TsOH is p-toluenesulfonic acid, and

DMAC is N,N-dimethylacetamide.

2. The method of claim 1, wherein the formic acid is used in an amount ranging from 5 to 30 equivalents based on the amount of the cefdinir intermediate of formula (II).

3. The method of claim 1, wherein sulfuric acid is used in an amount ranging from 2 to 5 equivalents based on the amount of the cefdinir intermediate of formula (II).

4. The method of claim 1, wherein the solvent is selected from the group consisting of acetonitrile, diethyl ether, tetrahydrofuran, 1,4-dioxane, ethyl acetate, methylene chloride, chloroform, isopropanol, ethanol and a mixture thereof.

5. The method of claim 1, wherein the solvent is acetonitrile.

6. A method of preparing cefdinir of formula (Ill) which comprises reacting the crystalline sulfuric acid salt of cefdinir of formula (I) with a base in a solvent:

7. The method of claim 6, wherein the solvent is selected from the group consisting of water, ethanol, methanol, acetonitrile, 1,4-dioxane, isopropanol, acetone, methylethylketone, methylisobutylketone and a mixture thereof.

8. The method of claim 6, wherein the base is selected from the group consisting of aqueous ammonia, sodium hydroxide, potassium hydroxide, sodium carbonate, potassium carbonate, sodium bicarbonate, potassium bicarbonate, sodium acetate, potassium acetate, sodium ethylhexanoate, triethylamine, diisopropylethylamine, dimethylethylamine, tributylamine, pyridine, dimethylbenzylamine, triethanolamine, dimethylaminopyridine and a mixture thereof.

9. The method of claim 8, wherein the base is sodium acetate.

\* \* \* \* \*